United States Patent
Yelisyeyev

(10) Patent No.: US 11,497,429 B2
(45) Date of Patent: Nov. 15, 2022

(54) ITERATIVE PROCESS FOR CALIBRATING A DIRECT NEURAL INTERFACE

(71) Applicant: COMMISSARIAT A L'ENERGIE ATOMIQUE ET AUX ENERGIES ALTERNATIVES, Paris (FR)

(72) Inventor: Andriy Yelisyeyev, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 714 days.

(21) Appl. No.: 16/473,516

(22) PCT Filed: Dec. 22, 2017

(86) PCT No.: PCT/FR2017/053818
§ 371 (c)(1),
(2) Date: Jun. 25, 2019

(87) PCT Pub. No.: WO2018/122518
PCT Pub. Date: Jul. 5, 2018

(65) Prior Publication Data
US 2019/0320924 A1    Oct. 24, 2019

(30) Foreign Application Priority Data

Dec. 28, 2016   (FR) ...................................... 1663473

(51) Int. Cl.
*A61B 5/30* (2021.01)
*A61B 5/316* (2021.01)
(Continued)

(52) U.S. Cl.
CPC ................ *A61B 5/316* (2021.01); *A61B 5/24* (2021.01); *A61B 5/245* (2021.01); *A61B 5/291* (2021.01);
(Continued)

(58) Field of Classification Search
CPC ......... A61B 5/316; A61B 5/245; A61B 5/291; A61B 5/24; A61H 3/00; G05B 13/048; G06F 3/015
See application file for complete search history.

(56) References Cited

U.S. PATENT DOCUMENTS 9,480,583 B2    11/2016  Aksenova et al.
2014/0031952 A1*  1/2014  Harshbarger ........ A61B 5/7264
                                                     623/25

OTHER PUBLICATIONS

International Search Report dated Mar. 23, 2018 in PCT/FR2017/053818 filed Dec. 22, 2017.

* cited by examiner

*Primary Examiner* — Curtis B Odom
(74) *Attorney, Agent, or Firm* — Oblon, McClelland, Maier & Neustadt, L.L.P.

(57) ABSTRACT

The subject of the invention is a method for calibrating a direct neural interface. The calibration is performed by considering a so-called input calibration tensor, formed on the basis of measured electrophysiological signals and so-called output calibration tensor, formed on the basis of measured output signals. The method comprises the application of a least squares multivariate regression implemented by considering a covariance tensor and a cross-covariance tensor which are established on the basis of input and output calibration tensors corresponding to a current calibration period. The method takes into account covariance and cross-covariance tensors established during an earlier calibration period prior to the current calibration period, these tensors being weighted by a forget factor.

11 Claims, 3 Drawing Sheets

(51) Int. Cl.
*A61H 3/00* (2006.01)
*G05B 13/04* (2006.01)
*G06F 3/01* (2006.01)
*A61B 5/24* (2021.01)
*A61B 5/245* (2021.01)
*A61B 5/291* (2021.01)
*A61B 5/374* (2021.01)

(52) U.S. Cl.
CPC ............. *A61H 3/00* (2013.01); *G05B 13/048* (2013.01); *G06F 3/015* (2013.01); *A61B 5/374* (2021.01); *A61B 2560/0223* (2013.01); *A61H 2230/105* (2013.01)

ITERATIVE PROCESS FOR CALIBRATING A DIRECT NEURAL INTERFACE

TECHNICAL FIELD

The invention relates to a direct neural interface, usually referred to by the English acronym BCI, standing for Brain Computer Interface, to allow the control of an automated effector, for example a robot or an exoskeleton, by cortical electrophysiological signals.

PRIOR ART

The field of direct neural interfaces is developing rapidly and appears to be an appealing solution for enabling the handicapped to control effectors by thought. It entails recording, generally with the aid of cortical electrodes, electrophysiological signals. The latter are processed by algorithms making it possible to extract a control signal, to control effectors. The control signal can allow the driving of an exoskeleton, of a computer or of a robot, so as to provide assistance to the user. The algorithms implemented allow translation of an instruction given by the user, this instruction being sensed, by the electrodes, in the form of signals termed electrophysiological since they are representative of the electrical activity of the neurons. This electrical activity is generally measured at the level of the cortex, by means of cortical electrodes disposed in the braincase. It can also be measured by electroencephalography electrodes, which are less intrusive since they are disposed on the scalp, but also less efficacious, in particular at the spatial resolution level. Another solution is to record the electrophysiological signals by magnetoencephalography, this requiring a dedicated facility.

The algorithms implemented are generally based on a predictive model. The predictive model uses input data, obtained by preprocessing the recorded electrophysiological signals. The input data are generally multidimensional, and comprise:
- a spatial component, representative of the spatial origin of the electrophysiological signal;
- a frequency component, representative of the intensity of the electrophysiological signal in various frequency bands;
- a temporal component, representative of the temporal evolution of the electrophysiological signal, each electrophysiological signal being acquired according to a high sampling frequency, typically a few kHz, during an acquisition time interval of a few hundred milliseconds to a few seconds. The acquisition time interval is generally referred to by the term "epoch".

These various components form a block of multidimensional data, comprising a large number of data, that must be processed in real time or in quasi-real time to obtain an output signal representative of an action controlled by the user. The data measured, at each acquisition time interval, can be grouped together in the form of a tensor of dimension 3, so-called input tensor, each dimension corresponding to a component mentioned hereinabove. Having regard to the significant number of data to be processed, predictive models based on algorithms for reducing the number of data have been implemented. U.S. Pat. No. 9,480,583 describes the application of a multivariate partial least squares linear regression scheme making it possible to establish a control signal on the basis of recorded electrophysiological signals. Such a scheme is known by the acronym "NPLS" or by the term "N-way Partial Least Squares". The application of such a scheme has also been described in the publication Eliseyev A, Aksenova T (2013) "Recursive N-way Partial Least Squares for Brain Computer Interface" PlOS ONE July 2013, Volume 8 Issue 7 e69962. Such a scheme is also described in the document Yelisyeyev A "Brain-Computer Interface with cortical electrical activity recording" Human health and pathology, University of Grenoble, 2011.

This scheme makes it possible to form a predictive model based on a calibration phase. The calibration phase is carried out on the basis of an input calibration tensor, comprising data representative of electrophysiological signals measured during various epochs, termed calibration input data. To each epoch there corresponds output data, representative of the control signal for the effector or of a state of the effector, the output data over all the epochs forming calibration output data.

The inventors have found that on account of the variability of the brain, the duration of validity of a predictive model is limited and that it is necessary to undertake regular updates. This involves the implementation of calibration phases spaced over time, so as to acquire calibration data. Such an update may require the manipulation of a very significant number of data, combining the data of an earlier calibration and the data of a new calibration. They have proposed a calibration method, allowing an update of the prediction model, while implementing a reasonable amount of data. The calculation power necessary for the update is then reduced, as is the duration of the update.

DISCLOSURE OF THE INVENTION

A first subject of the invention is a method for calibrating a direct neural interface, the interface being able to acquire electrophysiological signals and to form an input tensor on the basis of the electrophysiological signals acquired, so as to establish, with the aid of a predictive model, an output tensor, intended to control an effector, the predictive model being obtained by calibration, the calibration comprising the following steps:
- a) acquisition of so-called input electrophysiological calibration signals to obtain a so-called input calibration tensor, each electrophysiological signal being representative of neural activity during calibration;
- b) acquisition of so-called output calibration signals to obtain a so-called output calibration tensor, each output calibration signal being representative of a control signal for the effector or of a state of the effector during calibration, the output calibration signals being acquired, preferably, simultaneously with the input calibration electrophysiological signals;
- c) calculation of a covariance tensor, representing a covariance of the input calibration tensor;
- d) calculation of a cross-covariance tensor representing a covariance of the input calibration tensor and of the output calibration tensor;
- e) application of a partial least squares multivariate regression on the basis of the covariance tensor obtained in step c) and of the cross-covariance tensor obtained during step d) so as to obtain a predictive model, as well as calibration parameters;

steps a) to e) being implemented during a current calibration period, the method being such that after a first calibration period,
- step c) comprises a taking into account of the covariance tensor calculated in the course of an earlier calibration period, and weighted by a forget factor;

step d) comprises a taking into account of the cross-covariance tensor calculated in the course of the earlier calibration period, and weighted by the forget factor;

step e) comprises a taking into account of calibration parameters resulting from the earlier calibration period.

The forget factor can be a positive real lying strictly between 0 and 1.

During step e), the calibration parameters can comprise a collection of projection vectors, so that after the first calibration period, step e) comprises a taking into account of a collection of projection vectors resulting from the earlier calibration.

During step e) the partial least squares multivariate regression can be performed according to several iterations, to each iteration there corresponding an iteration rank, each iteration generating a model, so-called predictive model, making it possible to estimate a tensor, so-called output tensor, on the basis of an input tensor, the input tensor being formed on the basis of electrophysiological signals acquired at various instants;

the output tensor being formed of data of outputs intended to form control signals to control the effector.

The predictive model can comprise a so-called prediction matrix.

The method can comprise a determination of a so-called optimal iteration rank, the determination being carried out according to the following steps:

taking into account of an input calibration tensor and of an output calibration tensor corresponding to the current calibration period;

taking into account of predictive models respectively associated with various iteration ranks of the multivariate regression performed during the earlier calibration period;

application of each predictive model to the input calibration tensor of the current calibration period, so as to obtain an estimation of the output calibration tensor of the current calibration period, each estimation being associated with the rank of the iteration, corresponding to the predictive model, on the basis of which the estimation is performed;

comparison, for each iteration rank, of each estimation obtained during the previous step, with the output calibration tensor of the current calibration period;

determination of a, so-called optimal, iteration rank as a function of each comparison. The optimal iteration rank is in particular the one for which the estimation is closest to the output calibration tensor.

Another subject of the invention is a method of controlling an effector through a direct neural interface, comprising the following steps:

i) acquisition of electrophysiological signals produced in the cortex of an individual;

ii) processing of the electrophysiological signals, to form input data, assembled according to an input tensor;

iii) application of a predictive model to the input tensor so as to estimate an output tensor;

iv) formation of a control signal for the effector on the basis of the output tensor;

the method being characterized in that during step iii) the predictive model is determined by a calibration carried out according to a calibration method such as described in the patent application.

The output tensor can correspond to a state of the effector desired by the user generating the electrophysiological signals. In this case, the control signals make it possible to configure the effector according to the state thus estimated.

During step iii), it is possible to apply the predictive model corresponding to the optimal iteration rank (F*) previously determined.

A third subject of the invention is a direct neural interface, comprising:

sensors, able to acquire electrophysiological signals representative of a cortical activity;

a processor, for processing said electrophysiological signals;

an effector, configured to be actuated by a control signal generated by the processor;

the processor being configured to implement steps ii) to iv) of a method according to the second subject of the invention, on the basis of the electrophysiological signals acquired by the sensors. The sensors can be cortical electrodes, electroencephalography electrodes or magnetoencephalography sensors.

Other advantages and characteristics will emerge more clearly from the description which follows of particular embodiments of the invention which are given by way of nonlimiting examples and are represented in the figures listed hereinbelow.

FIGURES

DISCLOSURE OF PARTICULAR EMBODIMENTS

Figure 1:
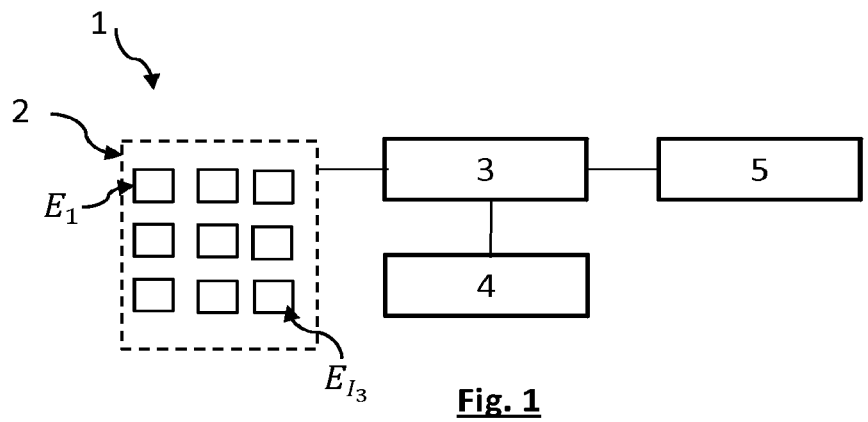
FIG. 1 shows a representation of the neural interface.

FIG. 1 represents the main elements of a neural interface 1 according to the invention. It entails a device comprising sensors 2, allowing the acquisition of electrophysiological signals representative of a neural activity. The sensors 2 are for example cortical electrodes. The sensors 2 are linked to a processor 3, by a wired or wireless link. The processor 3 is able to execute instructions coded in a memory 4. These instructions comprise in particular the algorithms described hereinafter. By implementing these instructions, the processor generates a control signal intended to drive an effector 5.

The effector 5 is an actuator able to perform an action under the effect of the control signal which is addressed to it. It may entail an exoskeleton, a robot, or a computer. The effector is then controlled by the electrophysiological signals acquired by the cortical electrodes 2, via an algorithm coded in the memory 4 and implemented by the processor 3. The device 1 is a direct neural interface, in the sense that it allows the control of the effector 5 by the electrophysiological signals measured by the sensors 2. The electrophysiological signals can be acquired by cortical electrodes placed in contact with the cortex, magnetoencephalography sensors or electroencephalograph electrodes.

As indicated in conjunction with the prior art, the control signal is formed by the processor 3 on the basis of the electrophysiological signals, grouped together, after preprocessing, according to a tensor, the so-called input tensor, by implementing a predictive model. The predictive model generates an output tensor, grouping together data, so-called output data, allowing the control of the effector 5. The predictive model forms the subject of learning, or calibration, during which the control signal, the so-called output signal, is trained.

In this example, the electrophysiological signals $S_1 \ldots S_{I_3}$, generated by an individual, are acquired by a number $I_3$ of cortical electrodes $E_1 \ldots E_{I_3}$ distributed on the surface of the cortex of said individual. $I_3$ is for example equal to 64. Each electrophysiological signal is representative of a cortical activity. The electrophysiological signals are acquired according to a sampling frequency of 1 KHz and are assembled as blocks of input data $\underline{x}(n)$ of a sliding duration equal to 1 second, each block corresponding to an observation window, or epoch. Each block of data is offset from the following block and from the precedent block by 100 ms. The electrophysiological signals acquired form the subject of a preprocessing before being grouped together according to an input tensor.

Each electrophysiological signal acquired by an electrode forms for example the subject of a frequency analysis according to $I_2$ frequency bands. For example, $I_2=15$. The frequency bands lie for example between 10 kHz and 150 kHz. The frequency analysis may be for example a wavelet transform.

Each electrophysiological signal can also form the subject of a decimation, so as to extend over $I_1$ time increments. For example, $I_1=10$.

The electrophysiological signals, after preprocessing (frequency analysis and decimation) are grouped into blocks of input data. Each block of input data $\underline{x}(n)$, corresponding to an instant n, is three-dimensional, and of dimension $I_1 \times I_2 \times I_3$. The blocks of input data $\underline{x}(n)$ can be grouped into a tensor $\underline{X}$, the so-called input tensor, grouping together a number N consecutive blocks of input data $\underline{x}(n)$. The input tensor is of dimension $N \times I_1 \times I_2 \times I_3$.

To each input data block x(n) there corresponds a control signal $\underline{y}(n)$, representing the control to be addressed to effectors at the instant n. As indicated previously, a predictive model makes it possible, on the basis of the input tensor $\underline{X}$, to obtain a so-called output tensor $\underline{Y}$. The output tensor groups together N consecutive blocks of output data $\underline{y}(n)$, in such a way that each block of input data $\underline{x}(n)$ is associated with a block of data output $\underline{y}(n)$, the block of output data allows the formation of the control signal for one or more effectors. The output tensor can correspond to a state of the effector, for example a position of the effector, such as desired by the individual generating the electrophysiological signals. The control signals are then adapted to configure the effector according to this state.

The dimension of each block of output data can vary according to typical cases. In the example considered, each output block drives three articulations of an arm, in this instance the wrist, the elbow and the shoulder, with three degrees of freedom per articulations. Each output block $\underline{y}(n)$ is therefore a 3×3 matrix, corresponding to the state of the three articulations.

Figure 2A:
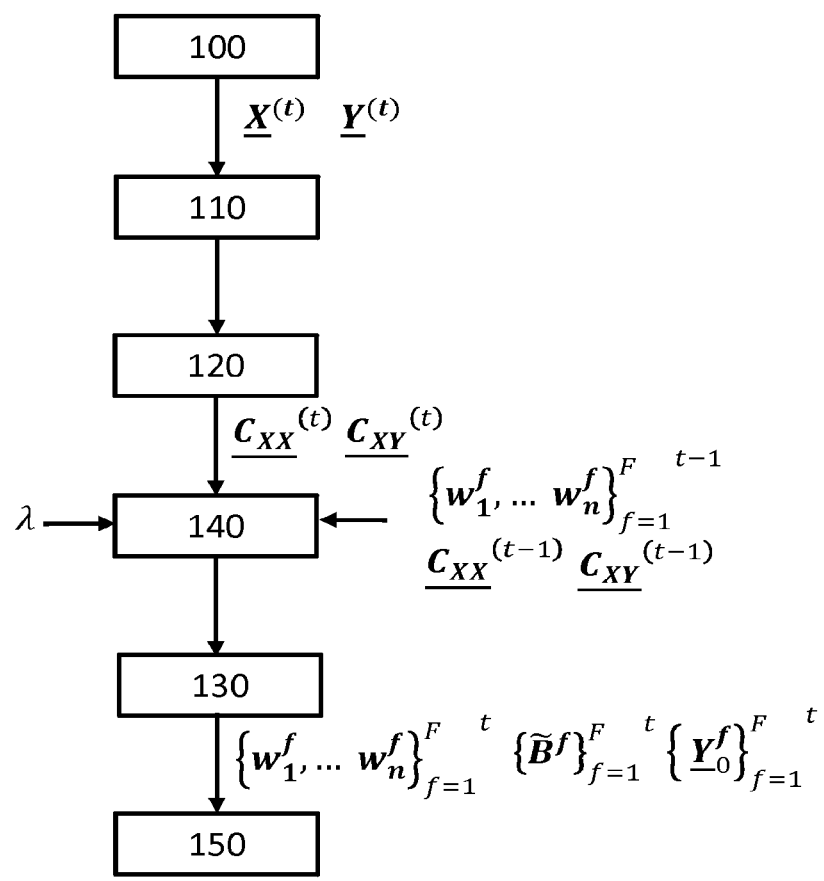
FIG. 2A represents the main steps of a calibration method.

The establishment of a predictive model according to the invention is now described in conjunction with FIG. 2A. The predictive model is produced in the course of a calibration phase, in the course of which the output signal, that is to say the control signal for the effector 5, or the state of the effector 5, is trained. For example, the individual is asked to perform a particular movement, during which electrophysiological signals are acquired. Thus, the input calibration data blocks $\underline{x}(n)$ are measured whilst each output calibration data block $\underline{y}(n)$, that is to say the state of the effector 5, is also measured or known.

The output calibration signals are either measured, or imposed, but they are known, in contradistinction to the phase of use of the direct neural interface, in the course of which the output signals are estimated on the basis of the input electrophysiological signals. The output calibration signals are representative of a control signal for the effector, or of a state of the effector, during the calibration. For example, a trajectory is measured or imposed on the effector, in which case the output calibration data represent the various positions of the effector during the trajectory, each position corresponding to a state of the effector. It is also possible to observe the behavior of the individual and the intentional actuation, by the latter, of the effector, in which case the output calibration data correspond to the control signal for the effector or to the state of the effector (actuated or non-actuated). For example, as described in patent U.S. Pat. No. 9,480,583, the effector is a pedal and the output calibration signal represents the actuation of the pedal by the individual.

The input calibration data constitute a so-called calibration input tensor $\underline{X}^{(t)}$ while the output calibration data form an output calibration tensor $\underline{Y}^{(t)}$. t designates a time period, the so-called calibration period, at which the calibration input and output data are acquired, the input and output calibration data preferably being acquired simultaneously.

Each input calibration block $\underline{x}(n)$ has dimension $I_1 \times \ldots \times I_k$: each of its coordinates is denoted $x_{n, I_1 \times \ldots \times I_k}$. In this example, k=3.

Each output calibration block $\underline{y}(n)$ has dimension $J_1 \times \ldots \times J_m$: each of its coordinates is denoted $y_{n, J_1 \times \ldots \times J_m}$. In this example, m=2.

Step 100: constitution of the calibration tensors $\underline{X}^{(t)}$ and $\underline{Y}^{(t)}$.

The input tensor can comprise a number N of input calibration and of calibration output data blocks $\underline{x}(n)$ and $\underline{y}(n)$.

The dimension of the input calibration tensor $\underline{X}^{(t)}$ is $N \times I_1 \times \ldots \times I_k$.

The dimension of the output calibration tensor $\underline{Y}^{(t)}$ is $\times J_1 \times \ldots \times J_m$.

One of the particularities of the calibration is that after a first calibration period, t>1, it takes into account the earlier calibration tensors $\underline{X}^{(t-1)}$ and $\underline{Y}^{(t-1)}$, in the form of covariance and cross-covariance tensors. Stated otherwise, during a first calibration, corresponding to t=1, the calibration algorithm is implemented on the basis of the first calibration tensors $\underline{X}^{(t=1)}$ and $\underline{Y}^{(t=1)}$. During the following calibrations, account is taken of the, so-called current, calibration tensors acquired at a period t, the so-called current period, during which each calibration is performed. These calibrations take account of the covariance tensors established on the basis of the earlier calibration tensors $\underline{X}^{(t-1)}$, $\underline{Y}^{(t-1)}$ obtained at an earlier calibration period prior to the current period. The contribution of the earlier calibration tensors is however weighted by a forget factor $\lambda$, as described in conjunction with step 140.

Step 110: normalization: the calibration tensors $\underline{X}^{(t)}$ and $\underline{Y}^{(t)}$ are preferentially normalized, in such a way that each of their terms is centered and reduced with respect to an average value and to a standard deviation. Accordingly, a so-called effective number of observations is determined: $N^{(t)} = \lambda N^{(t-1)} + N^{(t)}$ and a weighted sum $$S^t_{x_{i_1, \ldots, i_k}}$$

and a weighted quadratic sum $$S^{2t}_{x_{i_1,\ldots,i_k}}$$

are calculated respectively according to the expressions:

$$S^t_{x_{i_1,\ldots,i_k}} = \lambda \sum_{n=1}^{N^{(t)}-1} x^{t-1}_{n,i_1,\ldots,i_k} + \sum_{n=1}^{N^{(t)}} x^t_{n,i_1,\ldots,i_k}; \quad (1)$$

$$S^{2t}_{x_{i_1,\ldots,i_k}} = \lambda \sum_{n=1}^{N^{(t)}-1} \left(x^{t-1}_{n,i_1,\ldots,i_k}\right)^2 + \sum_{n=1}^{N^{(t)}} \left(x^t_{n,i_1,\ldots,i_k}\right)^2; \quad (2)$$

where $x_{n,i_1,\ldots,i_k}^t$ designates each term of the input calibration tensor $\underline{X}^{(t)}$ During the first calibration (t=1), the first term of each expression is zero.

It is then possible to establish an average value $$\mu^t_{x_{i_1,\ldots,i_k}}$$

and a standard deviation $$\sigma^t_{x_{i_1,\ldots,i_k}}$$

of the terms $x_{n,i_1,\ldots,i_k}^t$ making up the input tensor $\underline{X}^{(t)}$ according to the expressions:

$$\mu^t_{x_{i_1,\ldots,i_k}} = \frac{S^t_{x_{i_1,\ldots,i_k}}}{N^{(t)}} \text{ and} \quad (3)$$

$$\sigma^t_{x_{i_1,\ldots,i_k}} = \sqrt{\frac{S^{2t}_{x_{i_1,\ldots,i_k}} - \frac{\left(S^t_{x_{i_1,\ldots,i_k}}\right)^2}{N^{(t)}}}{N^{(t)} - 1}} \quad (4)$$

In an identical manner, it is possible to establish an average and a standard deviation of the terms $y_{n,j_1,\ldots,j_m}^t$ of the output tensor $\underline{Y}^{(t)}$ according to the expressions:

$$\mu^t_{y_{j_1,\ldots,j_m}} = \frac{S^t_{y_{j_1,\ldots,j_m}}}{N^{(t)}} \text{ and} \quad (5)$$

$$\sigma^t_{y_{j_1,\ldots,j_m}} = \sqrt{\frac{S^{2t}_{y_{j_1,\ldots,j_m}} - \frac{\left(S^t_{y_{j_1,\ldots,j_m}}\right)^2}{N^{(t)}}}{N^{(t)} - 1}} \quad (6)$$

The normalization consists in centering and reducing each term $x_{n,i_1,\ldots,i_k}^t$ and $y_{n,j_1,\ldots,j_m}^t$ in such a way that:

$$x^t_{n,i_1,\ldots,i_k} = \frac{x^t_{n,i_1,\ldots,i_k} - \mu^t_{x_{i_1,\ldots,i_k}}}{\sigma^t_{x_{i_1,\ldots,i_k}}} \quad (7)$$

$$y^t_{n,j_1,\ldots,j_m} = \frac{y^t_{n,j_1,\ldots,j_m} - \mu^t_{y_{j_1,\ldots,j_m}}}{\sigma^t_{y_{j_1,\ldots,j_m}}} \quad (8)$$

Step 120: calculation of the covariance tensor and of the cross-covariance tensor.

The covariance tensor is:

$$\underline{C}_{XX}^{(t)} = \underline{X}^{(t)} \times_1 \underline{X}^{(t)} \quad (10)$$

$$\underline{C}_{XY}^{(t)} = \underline{X}^{(t)} \times_1 \underline{Y}^{(t)} \quad (11)$$

$\times_1$ designates the tensor product according to mode 1, described in the literature, in particular in the thesis mentioned in the prior art.

Step 130: taking into account of a previous calibration.

The covariance and cross-covariance tensors are modified, by taking into account covariance and cross-covariance tensors relating to an earlier calibration period, this earlier period being denoted t−1.

$$\underline{C}_{XX}^{(t)} = \lambda \underline{C}_{XX}^{(t-1)} + \underline{X}^{(t)} \times_1 \underline{X}^{(t)} \quad (12)$$

$$\underline{C}_{XY}^{(t)} = \lambda \underline{C}_{XY}^{(t-1)} + \underline{X}^{(t)} \times_1 \underline{Y}^{(t)} \quad (13)$$

This step is a key step of the method, since it allows account to be taken of data used during a previous calibration phase, the taking into account of this history being weighted by a forget factor $\lambda$. The forget factor $\lambda$ is a real lying strictly between 0 and 1.

Thus, when a calibration is carried out at a current calibration period t, it takes account of a previous calibration, carried out at an earlier calibration period t−1. The method thus makes it possible to perform an updating of calibrations, each calibration taking into account a calibration performed previously. The taking into account of the history is weighted by the forget factor $\lambda$. The smaller it is, the less the history is taken into account.

During the first calibration period, (t=1), $\underline{C}_{XX}^{(t=1)} = \underline{X}^{(t=1)} \times_1 \underline{X}^{(t=1)}$ and $\underline{C}_{XY}^{(t=1)} = \underline{X}^{(t=1)} \times_1 \underline{Y}^{(t=1)}$.

Step 140: updating of the predictive model

In the course of this step, the predictive model is updated by applying an algorithm known by the acronym NPLS (N-Partial Least Squares), signifying partial least squares multivariate regression, to the cross-covariance and covariance tensors resulting from step 130. The algorithm followed is an iterative algorithm, according to the principles described in the publication Dayal B. "Improved PLS Algorithms", Journal of Chemometrics, Vol. 11, 73-85 (1997), and more precisely the modified algorithm number 2 appended to said publication. This iterative algorithm makes it possible to obtain, at each iteration f:

- a set of projection vectors, $w_1^f, \ldots w_k^f$. The vector $w_1^f$ is of dimension $I_1$, the vector $w_2^f$ is of dimension $I_2 \ldots$ the vector the vector $w_k^f$ is of dimension $I_k$. The set of iterations makes it possible to form sets of projection vectors $\{w_1^f, \ldots w_k^f\}_{f=1}^{F^t}$ corresponding to the calibration period t. These projection vectors allow projection of the input calibration tensor into a latent variable space.
- a prediction matrix $\tilde{B}^f$, forming the predictive model, allowing an estimation $\hat{Y}$ of an output tensor $\underline{Y}$ on the basis of an input tensor $\underline{X}$. The set of iterations makes it possible to form a set of prediction matrices $\{\tilde{B}^f\}_{f=1}^{F^t}$ corresponding to the calibration period t.
- a so-called bias tensor $\underline{Y}_0^f$, also forming the predictive model. The set of iterations makes it possible to form a set of bias tensors $\{\underline{Y}_0^f\}_{f=1}^{F^t}$ corresponding to the calibration period t.

f is the rank of the iteration. It entails an integer lying between 1 and a maximum number of iteration F, the latter being for example equal to 200.

The detail of this step, and the obtaining of the magnitudes listed hereinabove, are described subsequently, in conjunction with FIG. 4 and steps 141 to 149 described hereinafter.

Subsequent to this step, one has a predictive model allowing the estimation $\hat{\underline{Y}}^f$ of an output tensor $\underline{Y}$ on the basis of an input tensor $\underline{X}$ according to the expression:

$$\hat{\underline{Y}}^f = \tilde{B}^f \underline{X} + \underline{Y}_0^f \quad (14)$$

The notation $\hat{\underline{Y}}^f$ designates the fact that the tensor $\hat{\underline{Y}}$ is estimated according to the predictive model, in this instance the matrix $\tilde{B}^f$ and the bias tensor $\underline{Y}_0^f$ that are defined in the course of iteration f.

It is noted that in contradistinction to the prior art, the input and output tensors allowing the implementation of the NPLS algorithm of are not input tensors $\underline{X}$ and $\underline{Y}$ obtained respectively with measured input and output calibration data blocks, as is described in patent U.S. Pat. No. 9,480,583. The invention implements:
- the tensor $\underline{C}_{XX}^{(t)}$, which expresses a covariance of the input calibration tensor $\underline{X}^{(t)}$, of dimension $I_1 \times \ldots \times I_k \times I_1 \times \ldots \times I_k$;
- the tensor $\underline{C}_{XY}^{(t)}$, which expresses a cross-covariance of the input calibration tensor $\underline{X}^{(t)}$ and of the output calibration tensor $\underline{Y}^{(t)}$, of dimension $I_1 \times \ldots \times I_k \times J_1 \times \ldots \times J_m$.

The dimension of the tensors on the basis of which the iterative calibration is carried out is therefore reduced with respect to the prior art, in which the input and output calibration tensors are respectively $\underline{X}^{(t)}$ and $\underline{Y}^{(t)}$, whose respective dimensions are $N \times I_1 \times \ldots \times I_k$ and $N \times J_1 \times \ldots \times J_m$.

Step 140 is carried out by incrementing the iteration rank f until a maximum iteration rank F is reached.

Step 150: end of algorithm. One then has a predictive model corresponding to each iteration rank f, calibrated on the basis of the calibration tensors $\underline{X}^{(t)}$ and $\underline{Y}^{(t)}$ the calibration being carried out with the aid of an earlier calibration tensor $\underline{X}^{(t-1)}$ and $\underline{Y}^{(t-1)}$, and more precisely with the aid of the covariance and cross-covariance tensors resulting from the earlier calibration.

The predictive calibration model can be updated on the basis of new calibration tensors $\underline{X}^{(t+1)}$ and $\underline{Y}^{(t+1)}$, by repeating steps 100 to 150, while incrementing the calibration period t.

The updating frequency is variable. The inventors have found that it is preferable to carry out, initially, various successive calibrations, by considering so-called initial calibration tensors $\underline{X}^{ini}$ and $\underline{Y}^{ini}$ of large dimension, with N=7000. Such calibration tensors are acquired according to a long initial calibration duration, that may for example last more than 10 minutes. Indeed, because of the decimation, each time increment is spaced 100 ms apart. An acquisition duration N=7000 corresponds to 7000 data blocks $\underline{x}(n)$ and $\underline{y}(n)$, acquired according to a sliding acquisition duration of 1 s, each block being offset from the previous or following block by 100 ms. In the course of the initial calibration, each tensor $\underline{X}^{ini}$ and $\underline{Y}^{ini}$ is segmented into 70 segments $\underline{X}^{(t=1)} \ldots \underline{X}^{(t=70)}$ and $\underline{Y}^{(t=1)} \ldots \underline{Y}^{(t=70)}$, or buffer, each segment comprising N=100 input and output calibration data blocks of $\underline{x}(n)$ and $\underline{y}(n)$. Each segment $\underline{X}^{(t)}$ and $\underline{Y}^{(t)}$ constitutes respectively an input and output calibration tensor. Thus, steps 100 to 150 hereinbelow are repeated successively, by considering each calibration tensor $\underline{X}^{(t)}$ and $\underline{Y}^{(t)}$ with $1 \leq t \leq 70$.

On completion of these 70 successive iterative calibrations, one has a robust prediction model, that can be updated regularly for example daily or several times a day, by a short calibration sequence, requiring few data blocks $\underline{x}(n)$ and $\underline{y}(n)$, for example N=100, which, in view of the duration of each block (1 s) and of the offset between each block (100 ms), corresponds to a duration of 10 seconds. During the calibration, the user performs predetermined movements, so as to train the state of the output effector.

Figure 2B:
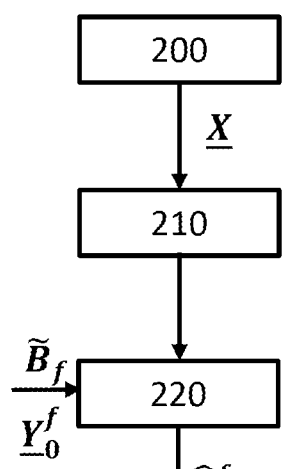
FIG. 2B represents the main steps of an estimation method using the calibration.

Between each calibration, the predictive model is used so as to estimate a state of the output tensor $\underline{Y}$ corresponding to an input tensor $\underline{X}$ by implementing the prediction expression (14). The main steps, described in FIG. 2B, are:

Step 200: acquisition of electrophysiological signals, pre-processing, obtaining of blocks of input data $\underline{x}(n)$ to form input tensor $\underline{X}$ Step 210: normalization of the input tensor, as described in conjunction with step 110.

Step 220: estimation of the output tensor, $\hat{\underline{Y}}^f$ by applying the expression (14). The use of the expression (14) requires the choice of an iteration rank f. This choice may be arbitrary, by being defined, generally once and for all, on the basis of preliminary trials. The output tensor thus estimated makes it possible to obtain control signals for controlling the effector 5. For example, the output tensor comprises a state of the effector desired by the user, and the control signals formed make it possible to attain this state.

The inventors have found that during the use of the predictive model, that is to say during the estimation of an output tensor $\hat{\underline{Y}}^f$ on the basis of a measured tensor $\underline{X}$, it is possible to determine an optimal iteration rank f, this optimal number being denoted F*

Figure 2C:
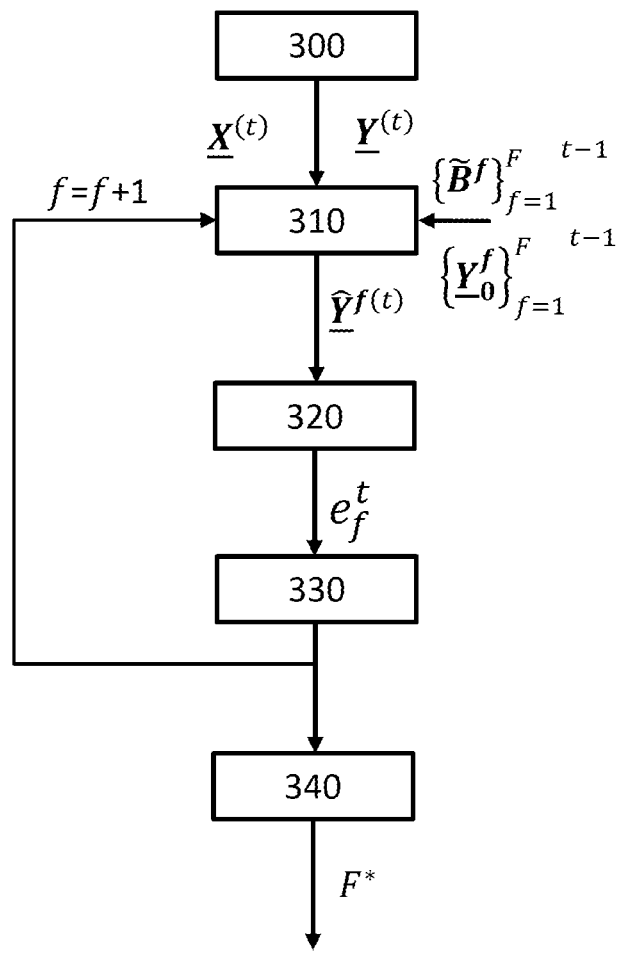
FIG. 2C represents the main steps of a method for determining an optimal number of iterations.

The main steps of the determination of the optimal number F* are described hereinafter in conjunction with FIG. 2C. Accordingly, the prediction matrices $\{\tilde{B}^f\}_{f=1}^{F-1}$, obtained during an earlier calibration, for example the previous calibration period t−1, are applied to calibration tensors $\underline{X}^{(t)}$ and $\underline{Y}^{(t)}$ corresponding to a calibration period t.

Step 300: initialization: f=1

Step 310: estimation $\hat{\underline{Y}}^{f(t)}$ of $\underline{Y}^{(t)}$ by using a prediction matrix $\tilde{B}^{f(t-1)}$ obtained during the previous calibration: $\hat{\underline{Y}}^{(t)} = \underline{X}^{(t)} \tilde{B}^{f(t-1)} + \underline{Y}_0^f$ Step 320: calculation of an error corresponding to iteration rank f, according to the expression:

$$e_f^t = \gamma e_f^{t-1} + \text{Error}(\hat{\underline{Y}}^{f(t)}, \underline{Y}^{(t)})$$

Error $(\hat{\underline{Y}}^f(t), \underline{Y}(t))$ represents an error of estimation of $\underline{Y}^{(t)}$, for example a quadratic error.

When t=1 (subsequent to the first calibration), $e_f^{t=1} = \text{Error}(\hat{\underline{Y}}^{f(t=1)}, \underline{Y}^{(t=1)})$. γ is a forget factor, independent of the forget factor γ considered during steps 100 to 150, lying strictly between 0 and 1.

Step 330: incrementation of f until f=F.

Step 340: determination of F*, such that $F^* = \arg\min_f e_f^t$.

According to this algorithm, the optimal iteration rank F* is adjusted after each updating of the predictive model, that is to say after each calibration period. This algorithm uses the input and output calibration tensors corresponding to a current calibration period t. It consists in obtaining an estimation of the output calibration tensor $\underline{Y}^{(t)}$, at the current period, by applying a predictive model, $(\{\tilde{B}^f\}_{f=1}^{F-1}, \{\underline{Y}_0^f\}_{f=1}^{F})$ arising from an earlier calibration period t=1, to the input=₁ calibration tensor at said current period $\underline{X}^{(t)}$. This makes it possible to improve the precision of the estimation of the output tensor during the application of the prediction model, according to expression (14). Thus, during the prediction steps, following the calibration at the current period t, the estimation of the output tensor is performed according to the expression:

$$\underline{\hat{Y}}^{f=F*} = \tilde{B}^{f=F*} \underline{X} + \underline{Y}_0^{f=F*} \quad (15)$$

The inventors have experimentally tested the algorithm for determining the optimal iteration rank F* after 70 calibrations, each calibration being carried out on a buffer of 100 data blocks (N=100). Accordingly, use has been made of calibration signals measured on a monkey, by a matrix of 64 cortical electrodes. The calibration signals measured by the electrodes are processed, so as to form the input calibration tensor $\underline{X}^{(t)}$ such as described previously. The movements of the 3 articulations of an arm of the monkey were recorded and form the output calibration tensor $\underline{Y}^{(t)}$.

Figure 3:
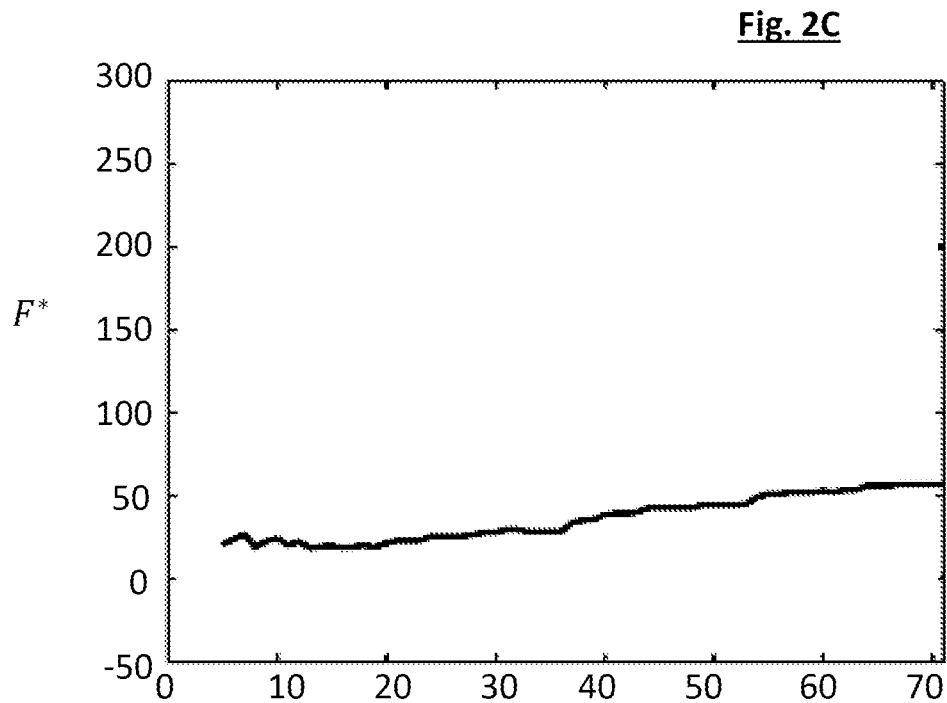
FIG. 3 represents an exemplary determination of an optimal rank of iterations.

FIG. 3 represents the evolution of the optimal number of iteration F* as a function of the various calibration, each calibration corresponding to an abscissa varying between 1 and 70. Each calibration is performed by taking a maximum number of iterations F, equal to 200. It is observed that the optimal number of iterations F* tends to 57.

Figure 4:
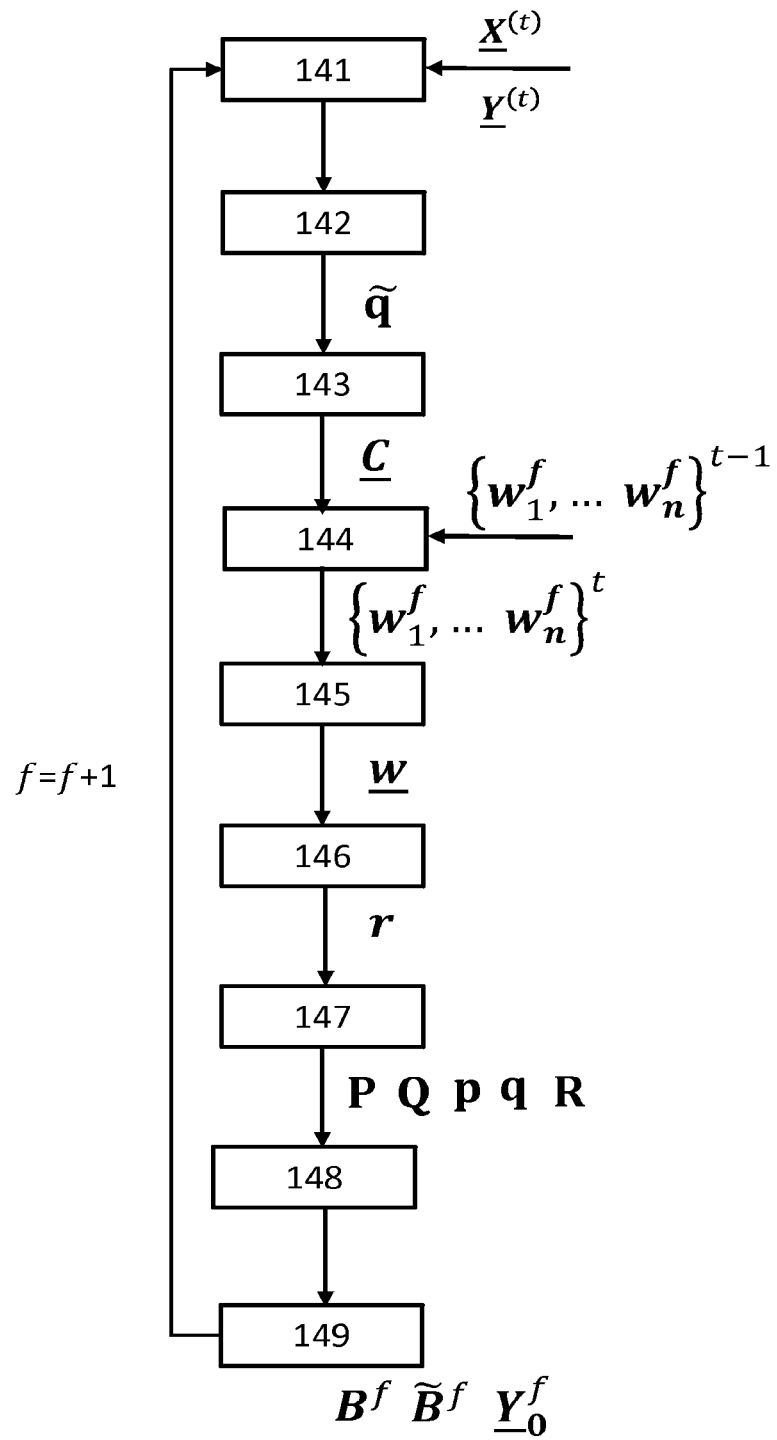
FIG. 4 represents the main sub-steps of a partial least squares multivariate linear regression.

FIG. 4 shows the main sub-steps of the step 140 of iterative updating of the predictive model. These steps are implemented iteratively, with an iteration rank f lying between 1 and F=200.

The input data are the input calibration $\underline{X}^{(t)}$ and output calibration $\underline{Y}^{(t)}$ tensors, as well as projection vectors $\{w_1^f \ldots w_k^f\}_{f=1}^{F-1}$ obtained subsequent to an earlier calibration. During the first calibration period t=1, these vectors are unit vectors.

Sub-step 141: Initialization: the internal matrices P, Q and R, defined hereinafter, are initialized to 0. $P \in \mathbb{R}^{(I_1 \cdots I_k) \times F}$; $Q \in \mathbb{R}^{(J_1 \cdots J_m) \times F}$; $R \in \mathbb{R}^{(I_1 \cdots I_k) \times F}$ Matrices $C_{XX}^{(t)} \in \mathbb{R}^{(I_1 \times \ldots \times I_k) \times (I_1 \times \ldots \times I_k)}$ are formed on the basis of the tensor $\underline{C}_{XX}^{(t)}$ and a matrix $C_{XY}^{(t)} \in \mathbb{R}^{(I_1 \times \ldots \times I_k) \times (J_1 \times \ldots \times J_m)}$ is formed on the basis of the tensor $\underline{C}_{XY}^{(t)}$. Steps 142 to 149 are thereafter performed in an iterative manner, f being the iteration rank.

Sub-step 142: Calculation of eigenvectors. If m>1 (m is the order of the output tensor), we determine the eigenvector $\tilde{q}$ corresponding to the highest eigenvalue of a matrix consisting of the product of the matrices $C_{XX}^{(t)^T} \times C_{XY}^{(t)}$. T designates the transpose operator. If m=1, the vector considered is $\tilde{q} = C_{XY}^{(t)}$ Sub-step 143: Formation of a tensor $\underline{C}$ on the basis of a matrix C formed by a matrix product $\bar{C}_{XY}^{(t)} \tilde{q}$: $\underline{C} = C_{XY}^{(t)} \tilde{q}$. $\underline{C} \in \mathbb{R}^{(I_1 \times \ldots \times I_k)}$ Sub-step 144: Decomposition by parallel factorial analysis of the tensor $\underline{C}$ formed during step 143 by considering the projection vectors $\{w_1^f, \ldots w_n^f\}^{t-1}$ of an earlier calibration, or the projection vectors initialized to 1 during the first calibration.

Sub-step 145: formation of a tensor $\underline{w} = w_1^f \circ \ldots \circ w_n^f$ and formation of a vector $w \in \mathbb{R}^{(I_1 \cdots I_k)}$ on the basis of the tensor $\underline{w}$. The vector w is thereafter normalized with respect to its norm.

Sub-step 146: formation of the regression vector.
We put r=w and we update the regression vector r by $r = r - [P(:,u)^T w R(:,u)]$ by varying u between 1 and f−1.

Sub-step 147: determination of internal vectors p and q, and updating of internal matrices P and Q and R.

$$p = \frac{(r^T C_{XX}^{(t)})^T}{r^T C_{XX}^{(t)} r} \text{ and } q = \frac{(r^T C_{XY}^{(t)})^T}{r^T C_{XX}^{(t)} r}$$

$P(:,f)=p$; $Q(:,f)=q$; $R(:,f)=r$

Sub-step 148: Deflation.

$$C_{XY}^{(t)} = C_{XY}^{(t)} - (r^T C_{XX}^{(t)} r) p q^T$$

Sub-step 149: Updating of the matrices formation of the prediction matrix $B^f$: $B^f = R(:,1:f) Q(:,1:f)^T$ The prediction matrix can form the subject of a normalization. Each term $b_{i_1,\ldots,i_k,j_1 \ldots j_m}^f$ of the matrix $B^f$ can be normalized in such a way that:

$$\tilde{b}_{i_1,\ldots,i_k,j_1 \ldots j_m}^f = b_{i_1,\ldots,i_k,j_1 \ldots j_m}^f \frac{\sigma_{y_{j_1,\ldots,j_m}}^t}{\sigma_{x_{i_1,\ldots,i_k}}^t}$$

$$\sigma_{y_{j_1,\ldots,j_m}}^t$$

and $$\sigma_{x_{i_1,\ldots,i_k}}^t$$

being defined in equations (6) and (4) respectively.

Each coefficient $\tilde{b}_{i_1,\ldots,i_k,j_1 \ldots j_m}^f$ forms the prediction matrix $\tilde{B}^f$ of the predictive model implemented in the prediction expression (14) or (15).

Moreover, the algorithm generates the bias tensor $\underline{Y}_0^f$, each term $$y_{0_{j_1,\ldots j_m}}^f$$

of which is defined by the expression:

$$y_{0_{j_1,\ldots j_m}}^f = \mu_{y_{j_1,\ldots,j_m}}^t - \sum_{i_1 \ldots i_k} \mu_{x_{i_1,\ldots,i_k}}^t \tilde{b}_{i_1 \ldots i_k, j_1 \ldots j_m}^f,$$

the quantities $$\mu_{y_{j_1,\ldots,j_m}}^t$$

and $$\mu_{x_{i_1,\ldots,i_k}}^t$$

being defined in expressions (4) and (3).

The output data of the algorithm are those described in conjunction with step 140.

The invention claimed is:

1. A method for calibrating a direct neural interface, the interface being configured to acquire electrophysiological signals, using sensors, and to form an input tensor therefrom, so as to establish, using a predictive model, an output tensor, the latter being intended to generate a control signal of an effector, the predictive model resulting from a calibration, the calibration comprising calibration periods, each calibration period comprising:

a) acquiring input electrophysiological calibration signals and forming an input calibration tensor therefrom, the electrophysiological calibration signals being produced by the cortex of an individual and measured by the sensors, the electrophysiological calibration signals being representative of neural activity during the calibration period;

b) acquiring output calibration signals and forming an output calibration tensor therefrom, each output calibration signal being representative of a control signal for the effector or of a state of the effector during the calibration;

c) calculating a covariance tensor, representing a covariance of the input calibration tensor;

d) calculating a cross-covariance tensor representing a covariance of the input calibration tensor and of the output calibration tensor;

e) applying a partial least squares multivariate regression on the basis of the covariance tensor obtained in c) and of the cross-covariance tensor obtained during d) so as to obtain a predictive model, as well as calibration parameters;

a) to e) being implemented during each calibration period; wherein, after a first calibration period, c) comprises taking into account of a covariance tensor resulting from an earlier calibration period, and weighted by a forget factor;

d) comprises taking into account of a cross-covariance tensor calculated resulting from the earlier calibration period and weighted by the forget factor;

e) comprises taking into account of calibration parameters resulting from the earlier calibration period, so that after the first calibration period, each calibration period provides an updated predictive model.

2. The method of claim 1, wherein the forget factor is a positive real number lying strictly between 0 and 1.

3. The method of claim 1, wherein during e), the calibration parameters comprise projection vectors, so that after the first calibration period, e) comprises a taking into account of projection vectors resulting from an earlier calibration.

4. The method of claim 1, wherein during e) the partial least squares multivariate regression is performed according to several iterations, to each iteration there corresponding an iteration rank, each iteration generating a predictive model, the predictive model being configured to provide an estimated output tensor, on the basis of an input tensor; and wherein:

the input tensor is formed using the electrophysiological signals acquired at various instants within a calibration period;

the estimated output tensor comprises data of outputs intended to form control signals to control the effector.

5. The method of claim 4, further comprising determining of an optimal iteration rank, the determination of the optimal iteration rank comprising:

taking into account an input calibration tensor and of an output calibration tensor corresponding to a current calibration period;

taking into account of the predictive models respectively associated with various iteration ranks of the partial least squares multivariate regression performed during an earlier calibration period;

applying each predictive model to the input calibration tensor of the current calibration period, so as to obtain an estimated the output calibration tensor of the current calibration period, each estimated the output calibration tensor being associated with the rank of the iteration corresponding to the predictive model on the basis of which the estimation is performed;

comparing, for each iteration rank, each estimated the output calibration tensor, with the output calibration tensor of the current calibration period; and determining of the optimal, iteration rank from each comparison.

6. The method of claim 1, wherein each sensor is one of:
a cortical electrode; or
a magnetoencephalography sensor; or
an electroencephalography electrode.

7. The method of claim 1, wherein the effector is an actuator configured to perform an action under the effect of the control signal.

8. The method of claim 7, wherein the effector is an exoskeleton or a robot or a computer.

9. A method of controlling an effector through a direct neural interface, comprising:

i) acquiring, using sensors, electrophysiological signals produced in the cortex of an individual, the electrophysiological signals being representative of a cortical activity;

ii) processing, using a processing unit, the electrophysiological signals, thereby to form input data, assembled according to an input tensor;

iii) applying a predictive model to the input tensor so as to estimate an output tensor iv) forming a control signal for the effector on the basis of the output tensor;

wherein during iii) the predictive model is determined by a calibration carried out according to a calibration method according to claim 1.

10. The method of claim 9, wherein during iii), the predictive model corresponding to an optimal iteration rank is applied, the optimal iteration rank being determined according taking into account an input calibration tensor and of an output calibration tensor;

taking into account of the predictive models respectively associated with various iteration ranks of the partial least squares multivariate regression performed during an earlier calibration period;

applying each predictive model to the input calibration tensor of the current calibration period, so as to obtain an estimated the output calibration tensor of the current calibration period, each estimated the output calibration tensor being associated with the rank of the iteration corresponding to the predictive model on the basis of which the estimation is performed;

comparing, for each iteration rank, each estimated the output calibration tensor, with the output calibration tensor of the current calibration period; and determining of the optimal, iteration rank from each comparison.

11. A direct neural interface, comprising:
sensors, configured to acquire electrophysiological signals representative of a cortical activity;
a processor, for processing the electrophysiological signals;
an effector, configured to be actuated by a control signal generated by the processor;
wherein the processor is configured to implement ii) to iv) of the method of claim 9, on the basis of the electrophysiological signals acquired by the sensors.

* * * * *